US005276219A

United States Patent [19]
Schwindeman et al.

[11] Patent Number: 5,276,219
[45] Date of Patent: Jan. 4, 1994

[54] PREPARATION OF LITHIUM ALKOXIDES

[75] Inventors: James A. Schwindeman, Charlotte; B. Troy Dover, Kings Mountain; Robert C. Morrison; Conrad W. Kamienski, both of Gastonia, all of N.C.

[73] Assignee: FMC Corporation, Philadelphia, Pa.

[21] Appl. No.: 973,116

[22] Filed: Nov. 6, 1992

[51] Int. Cl.$^5$ .............................................. C07C 31/30
[52] U.S. Cl. .................................................... 568/851
[58] Field of Search ........................................ 568/851

[56] References Cited

U.S. PATENT DOCUMENTS

| | | | |
|---|---|---|---|
| 2,761,880 | 9/1956 | Gerber et al. | 568/851 |
| 3,239,568 | 3/1966 | De Pree et al. | 568/851 |
| 3,761,529 | 9/1973 | Drahoslav et al. | 260/643 |
| 4,709,103 | 11/1987 | Surber | 568/851 |

OTHER PUBLICATIONS

Kamienske et al, J. Org. Chem., 30 (1965), pp. 3498-3504.
Dermer, Chem. Rev. 14 (1934) pp. 385-430.
Jones et al, J. Chem. Soc., 123 (1923) 3285-3295.
Cram et al, J. Am. Chem. Soc. 81 (1959) 5963-5987.
Lochmann et al Collection Czechoslov. Chem. Commun. 35 (1970) 733-736.

*Primary Examiner*—Marianne M. Cintins
*Assistant Examiner*—Rebecca Cook
*Attorney, Agent, or Firm*—Charles C. Fellows; Robert L. Andersen

[57] ABSTRACT

A process for producing clear, colorless solutions of branched lithium alkoxides containing 3 to 12 carbon atoms, in a polar reaction solvent, comprising reacting a dispersion of lithium metal having a particle size less than 300 microns with a minimum of 5 mole percent excess over stoichiometric of a branched alkyl alcohol containing 4 to 12 carbon atoms, in a polar reaction solvent as the reaction medium, at a temperature between 50° C. and the boiling point of the solvent in an inert atmosphere.

6 Claims, No Drawings

PREPARATION OF LITHIUM ALKOXIDES

This application concerns preparation of lithium tertiary alkoxides by the reaction of lithium metal with a tertiary alkyl alcohol in a polar reaction solvent solvent.

Lithium tertiary alkoxides are known to be useful as polymerization catalysts and in the synthesis of pharmaceutical compounds. Lithium alkoxides have been known and prepared in a variety of solvents for many years. For example, C. W. Kamienski and D. H. Lewis described their preparation and soluble properties in alcohols, hydrocarbons, and ethers (*J. Org. Chem*, 30, 3498 (1965). Other authors, e.g. O. C. Dermer, *Chem Rev*, 14,38 (1934); J. H. Jones and J. S. Thomas, *J. Chem. Soc.*, 123, 3284 (192 ) and D. J. Cram and coworkers; *J. Am. Chem Soc.*, 81, (1959), report the preparation of lithium alkoxides in alcohols and ethers but give no solubility data.

Lithium tert-butoxide is a commercial product and has found uses as a polymerization initiator and in synthetic applications, particularly in the preparation of anti-bacterial drugs, where it can be used to promote cyclizations to give beta lactam rings (see U.S. Pat. No. 5,075,439, to Pfizer, Inc.)

N. I. Kozlova et al, ZH. Neorg. Khein., 24(1), 192–9 (1979) have carried out physical studies on solubilities of the lithium and sodium tert-butoxide in tetrahydrofuran (THF). Lithium tert-butoxide was prepared in hexane, the solid product isolated and then dissolved in tetrahydrofuran. L. Lochmann et al, Collection Czechoslov. Chem. Commun., vol. 35,733 (1970), also describes the preparation of lithium tert-butoxide in tetrahydrofuran, but carry out the reaction between lithium metal and tert-butyl alcohol directly in this solvent. A patent by D. Lim et al (to the Czech Academy of Sciences), U.S. Pat. No. 3,761,529, describes a method for purifying alkali metal alkoxides by crystallation from polar solvents, such tetrahydrofuran. In Table I on page 734 of their paper entitled "Preparation of Some Alkoxides of Alkaline Metals", L. Lochmann, J. Coupek and D. Lim (collection Czechoslov. Chem. Commun. vol 36. 1970), state in footnote (b) to the conditions set forth for the preparation of lithium tert-butoxide, that "turbidity of THF solution is difficult to remove; this alkoxide is more conviently prepared in a hydrocarbon medium, e.g. heptane[17]." The entry in the table clearly shows that an excess of lithium metal over tert-butyl alcohol is employed.

We have unexpectedly noted that lithium metal, kept in contact with dry tetrahydrofuran for any significant length of time (from a few hours to longer either prior or after reaction with tert-butyl alcohol) causes the formation of suspensoid products which are difficult to filter and thus, to isolate the desired clear solutions. The presence of such difficult to remove suspensoids containing unreacted lithium metal, is often detrimental in subsequent reactions requiring the use of lithium tert-butoxide, especially when the cyclization of ketones, amides, esters, etc. is contemplated.

We have not found this filtration problem to exist when other lithium containing raw materials, such as lithium hydride or lithium amide, are used to generate lithium tert-butoxide. It is not clear what constitutes the nature of these unfilterable suspensoids, but it is believed that a slow surface reaction to some sort occurs between the lithium metal and tetrahydrofuran.

The present invention provides a process for producing clear, colorless solutions of branched lithium alkoxides containing 3 to 12 carbon atoms in a polar reaction solvent, such as tetahydrofuran. Lithium metal is reacted with a minimum of 5 mole percent excess of a branched alkyl alcohol such as tertiary butyl alcohol, in a polar reaction solvent as the reaction medium, at a temperature above 50° C. and in an inert atmosphere.

The lithium metal used in the process of the invention is usually in the form of a suspension, which after the mineral oil is removed by washing with a reaction media solvent, is introduced into the reactor, typically as a slurry in reaction solvent. The lithium metal is typically a commerically available dispersion containing an alloying amount of sodium (0.4 to 0.76 weight percent on the lithium), however pure lithium metal dispersions can be successfully employed. Preferably the lithium metal is used in particulate form preferably less than 300 microns in size and most preferably 10 to 300 microns in size. Coarser lithium metal can also be employed.

The alcohols useful in the practice of this invention are branched, monohydric alkyl alcohols containing 3 to 12 carbon atoms which includes iso-, secondary and tertiary alcohols or alkanols such as iso-propyl, sec-butanol, 4-methyl-2-pentanol, tert-butanol, tert-amylalcohol, 3-methyl-3-pentanol, 2,6-dimethyl-4-heptanol and the like. Also useful in the practice of this invention are 2-alkyl substituted monohydric alcohols exemplified by 2-methylpentanol and 2-ethylhexanol.

The process of the invention employs a lithium metal dispersion which are washed several times with a the solvent, such as tetrahydrofuran, which will also be used in the reactor, to remove the dispersion oil from the metal. Three washes are generally sufficient after which the dispersion is transferred in some or all of the the reaction solvent to the reactor and heated to 50° C. The alcohol, such as tertiary butyl alcohol is slowly fed to the reactor. As the alcohol is slowly fed to the reactor the temperature spontaneously rises to reflux, 66° C. in the case of tetrahydrofuran. About half way through the alcohol feed the temperature drops but the temperature is maintained at least at 50° C. After the alcohol feed is completed the reaction mixture is heated to reflux and maintained there for two to three hours to ensure completion of the reaction. When the reaction is complete the reaction mass is cooled to ambient temperature, the product is filtered, generally with the help of a filter aid medium, to give a clear, colorless 2 molar, in the case of lithium tertiary butoxide, solution in tetrahydrofuran.

We have now also unexpectedly noted that as long as there is a reaction occurring at the surface of the lithium metal e.g. with tert-butyl alcohol, this unfilterable suspensoid does not form, even at elevated temperatures. Thus, short contact times (an hour or less) between e.g. lithium metal powder and THF, coupled with the use of an excess of tert-butyl alcohol over lithium effectively prevents the formation of these unfilterable suspensoids, and allows for rapid reaction generating clear solutions of the desired lithium tert-butoxide in THF product.

Of equal importance then to short initial lithium metal/THF contact time is the use of an excess of tert-butyl alcohol over lithium metal. We have found that, at least 5 mole % excess of tert-butyl alcohol over lithium metal is desirable, and more preferred is at least a 10 mole % excess tert-butyl alcohol. A preferred range is 5–20 mole % excess of tert-butyl alcohol, with a most preferred range of 8–15 mole %. These levels of excess tert-butyl alcohol are sufficient to prevent the formation of the said difficult to filter suspensoids.

At the levels of concentration of lithium tert-butoxide in the 8–15 mole % excess normally employed, such excess tert-butyl alcohol levels are quite low, constituting in the order of only about 1–5 weight percent of such solution; such low amounts of free alcohol generally do not interfere in the synthetic applications which are the major end use for such solutions.

Also contemplated in our invention are various alcohols which form soluble lithium alkoxide in reactive solvent media such as tetrahydrofuran. Thus, iso-,beta-branched, secondary and tertiary alcohols of all kinds may be employed in reaction with lithium metal in tetrahydrofuran, such as, e.g., isobutyl alcohol, isopropanol, sec-butanol, tert-butanol (tert-butyl alcohol), tert-amyl alcohol, isoamyl alcohol, 2-methylpentanol, 2-ethylhexanol, 3,3-dimethylpentanol, and the like.

It is also contemplated to employ preferred excesses of these alcohols with other alkali metals, such as sodium and potassium.

Other means of preparing such tetahydrofuran solutions of lithium alkoxides are also contemplated, and included in the following:

(a) From lithium hydride:

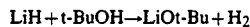
$$LiH + t\text{-}BuOH \rightarrow LiOt\text{-}Bu + H_2$$

(b) From lithium amide:

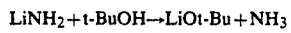
$$LiNH_2 + t\text{-}BuOH \rightarrow LiOt\text{-}Bu + NH_3$$

(c) From sodium or potassium tert-butoxide and lithium halides:

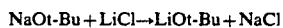
$$NaOt\text{-}Bu + LiCl \rightarrow LiOt\text{-}Bu + NaCl$$

(d) From lithium hydroxide:

$$LiOH + t\text{-}BuOH \rightarrow LiOt\text{-}Bu + H_2O$$

$H_2O$ removed by appropriate means to drive reaction
(e) From lithium methoxide:

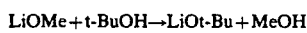
$$LiOMe + t\text{-}BuOH \rightarrow LiOt\text{-}Bu + MeOH$$

Methanol removed by appropriate means to drive reaction

Other lithium "reactive" solvents than tetrahydrofuran are also contemplated, such as e.g., 1,2-dimethoxyethane, methyltetrahydrofuran, tetrahydropyran, pyridine, and N,N,N',N'-tetramethyl ethylenediamine.

The process employs at least a 5 and preferably 10 mole percent excess of alcohol over the amount stoichiometric to lithium. Excess alcohol in amounts of 50 to 100 mole percent excess above stoichiometric can be employed, however an excess of 20 mole percent of tertiary butyl alcohol was used and this level did not provide a very significant increase in filtration rate. When less than 5 mole percent excess over stoichiometric of tertiary butyl alcohol is used the product is very difficult to filter.

The following examples further illustrate the invention.

EXAMPLE 1

Preparation of Lithium tert-Butoxide in Tetrahydrofuran Using Excess of tert-Butanol (8099)

A one liter, three-necked, cleaved Morton flask was fitted with a mechanical stirrer, a 250 ml pressure-equalizing addition funnel, and a Claisen adapter equipped with a reflux condenser, a thermocouple and an argon inlet. The apparatus was dried overnight at 125° C., assembled hot and allowed to cool to room temperature in a stream of Argon. Lithium dispersion, 8.75 grams (1.26 moles) was washed free of mineral oil by washing the dispersion three times with tetrahydrofuran, dried with argon and transferred to the flask with 450 ml of tetrahydrofuran. The resultant slurry was stirred at 400 revolutions per minute(rpm) and heated to 50° C. with a heating mantle, controlled by a temperature controller. Tertiary butyl alcohol, 103.03 grams (1.39 mole, 10.31% excess) and 70 ml tetrahydrofuran were mixed in the addition funnel. The tertiary butylalcohol feed was added dropwise. Hydrogen gas evolution began almost immediately and the temperature spontaneously increased and after addition of 15 ml of the alcohol solution the reflux temperature was attained. As the addition of the alcohol solution continued the reactor temperature slowly declined. Total feed time for the alcohol solution was 1 hour and 3 minutes. The reaction mixture was opaque/white at the end of the feed. Heat was applied to raise the reaction to reflux, the reaction mixture became less opaque as the heating proceeded. Gas continued to evolve after 2 hours at reflux. After 3 hours at reflux, the reaction mixture was still slightly hazy. The heat source was removed and the reaction mixture allowed to cool to room temperature. The product solution was transferred to a filter containing a filter aid and rapidly filtered under 2.5 PSI (17.2 kPa) argon pressure. The solution was allowed to cool to room temperature and then filtered. The solution filtered rapidly (2 minutes) at 2.5 psi of argon to give 625 ml. (522 g) of a clear, pale yellow liquid with no haze. The product solution contained 17.65 wt % (91.4% recovered yield) of lithium tert-butoxide. The molarity of the solution was 1.94M.

COMPARISON EXAMPLE A

Preparation of Lithium tert-Butoxide in Tetrahydrofuran Using an Excess of Lithium Metal (7591)

A weight of 5.6 grams (0.8 g. atoms) of lithium metal powder and 130 ml of tetrahydrofuran were placed in a reaction flask along with 5 ml of tert-butyl alcohol and the mixture heated to reflux. A solution of 40 ml (0.42 mole) of tert-butyl alcohol dissolved in an equal volume of tertrahydrofuran was then added dropwise to the refluxing mixture over a 1.5 hr period, and the product refluxed for a further 1.5 hr period of time. After cooling to room temperature, it was noted that the resulting pink reaction mixture would not settle, even after 3 days (week-end).

The mixture filtered only very slowly, and was complete only after filtration overnight (16 hours). A volume of 200 ml of a yellow, clear solution was obtained which contained no tert-butyl alcohol (by GLC). It was found to be 1.87 Molar lithium tert-butoxide (93.5% yield). The slowness of the filtration was believed to be due to a slow reaction occurring between lithium metal and tetrahydrofuran.

To prove this out, lithium metal powder and tetrahydrofuran (dried to 6 ppm Water) were stirred over a 4 hour period, then reacted normally with tert-butyl alcohol (10 mole % excess). After cooling of the reaction a slow filtration (4 hours) was noted. No filtration problems were noted when lithium tert-butoxide was prepared using heptane as solvent in place of tetrahydrofuran (C. W. Kamienski and D. H. Lewis, J. Org. Chem. 30, 3503 (1965).

COMPARISON EXAMPLE B

Preparation of Lithium tert-Butoxide in Tetrahydrofuran Using Lithium Hydride (7592)

In an attempt to avoid the slow filtration noted when an excess of lithium metal was employed (Comparative Example A), lithium hydride (excess) was substituted for lithium metal.

A weight of 21 grams (2.63 moles) of 30 mesh lithium hydride was covered with 700 ml of tetrahydrofuran and the mixture stirred and heated to reflux. Then, 206 ml, 163 g. (2.2 moles) of tert-butyl alcohol dissolved in 200 ml of tetrahydrofuran was added to the refluxing mixture over a 5 hr. period and then the mixture refluxed for an additional hour and cooled. Assay of the product solution showed that about 2% of unreacted tert-butyl alcohol remained (8.8% conversion). An additional 15 g (1.89 m) of lithium hydride was added and the mixture was heated and stirred at reflux for an additional 3-4 hrs. After this treatment, the tert-butyl alcohol content of the solution had dropped to 0.17% (99%).

The product mixture was found to filter rapidly to give 1020 ml of a pale yellow, clear solution which assayed 2.03 Molar in lithium tert-butoxide (94% recovered yield).

This example demonstrated that the presence of a large excess of lithium hydride does not inhibit the filtration of the product mixture, as does lithium metal.

Another run (4513) of this product made using only a 20% mole excess of lithium hydride also produced an easily filterable product in 95.6% yield (2.34M solution of lithium tert-butoxide in tetrahydrofuran.

COMPARISON EXAMPLE C

Preparation of Lithium tert-Butoxide in Tetrahydrofuran Using Lithium Amide in Large Excess A weight of 13.58 g (0.59 moles) of lithium amide, ground material—30 mesh, 97% pure, was transferred to a 250 ml flask under Argon and 100 ml of dry tetrahydrofuran added. To the stirred mixture was slowly added (15-30 min) 22 ml (18.5 g, 0.25 moles) of tert-butyl alcohol. Vigourous gas evolution was noted throughout the addition. When the gas evolution had subsided (about 1 hour after addition was complete), the mixture was heated to boiling to remove ammonia. After cooling, that product mixture was filtered easily to obtain 110 ml of a 1.87 Molar solution of lithium tert-butoxide (82% recovered yield). The solution still contained some ammonia.

EXAMPLE 2

Preparation of Lithium tert-Butoxide Via Interchange Between Sodium tert-Butoxide and Lithium Chloride (7943)

Dried lithium chloride by-product (0.85 moles) from a run of n-butyllithium was transferred with the aid of 350 ml of high purity heptane and 10 ml of Unocals SN 66/3 solvent to a 1 liter reaction flask. Sufficient sodium was added (19.6 g, 0.85 moles) in the form of small pieces to react with all the lithium chloride present. The mixture was heated to 100° C. and stirred vigorously until the sodium had formed particles the size of a fine sand. The mixture was then cooled without stirring to 37° C. A volume of 125 ml, 98 g (1.33 moles) of tert-butyl alcohol was added slowly to react with the sodium metal plus any excess lithium metal and butyllithium left in the lithium chloride by product "muds". The temperature of the reaction was gradually raised to reflux (85° C.) and the mixture stirred until there was no further evidence of reaction, (hydrogen evolution). Finally, an additional charge of tert-butyl alcohol equal to the above was added and the mixture heated at reflux for an additional 2 hrs. The residual tert-butyl alcohol was then distilled off as the heptane azeotrope. The mixture was then filtered hot (slow filtration), the residue washed once with 100 ml heptane plus 50 ml of tetrahydrofuran and then once with 100 ml of tetrahydrofuran. The total recovered alkalinity in the clear filtrates was 619 meq for 56% recovered yield of lithium tert-butoxide.

An improved product recovery can be realized by reacting the sodium with tert-butyl alcohol (in the presence of lithium chloride). Other sources of lithium chloride, anhydrous, may be employed.

What is claimed is:

1. A process for producing clear, colorless solutions of branched lithium alkoxides containing 3 to 12 carbon atoms, in a polar reaction solvent, comprising reacting a dispersion of lithium metal having a particle size less than 300 microns with a minimum of 5 mole percent excess over stoichiometric of a branched alkyl alcohol containing 3 to 12 carbon atoms, in a polar reaction solvent selected from the group consisting of tetrahydrofuran, methyl-tetrahydrofuran, tetrahydropyran, pyridine, N,N,N',N'-tetramethylethylenediamine and 1,2-dimethoxyethane as the reaction medium, at a temperature between 50° C. and the boiling point of the solvent in an inert atmosphere.

2. The process of claim 1 where in the branched alkyl alcohol is used in an amount of 5 to 50% in excess of stoichiometric based on the lithium metal used.

3. The process of claim 2 wherein the branched alkyl alcohol is used in an amount of 8 to 15 percent in excess over stoichiometric based on the lithium metal.

4. The process of claim 3 wherein the branched alkyl alcohol is selected from the group consisting of isopropanol, iso-butanol, secondary butanol, tertiary butanol, 4-methyl-2-pentanol, 3-methyl-3-pentanol, tertiary amyl alcohol, 2,6-dimethyl-4-neptanol, 2-ethylhexanol and 3,3 dimethyl-pentanol.

5. The process of claim 4 wherein the branched alkyl alcohol is tertiary butanol.

6. A process for producing clear, colorless solutions of branched lithium alkoxides containing 3 to 12 carbon atoms, in a polar reaction solvent, comprising reacting a dispersion of lithium metal having a particle size of 10 to 300 microns with an 8 to 15 mole percent excess over stoichiometric of tertiary butanol, at a temperature between 50° C. and 66° C. in tetrahydrofuran in an inert atmosphere.

* * * * *